United States Patent [19]

Cain

[11] Patent Number: 4,521,426

[45] Date of Patent: Jun. 4, 1985

[54] PESTICIDAL BICYCLOOXYHETEROCYCLYL AROYL UREAS

[75] Inventor: Paul A. Cain, Cary, N.C.

[73] Assignee: Union Carbide Corporation, Danbury, Conn.

[21] Appl. No.: 428,994

[22] Filed: Sep. 30, 1982

[51] Int. Cl.$^3$ .................... C07D 213/64; A01N 43/40
[52] U.S. Cl. .................................. 514/346; 546/297; 546/269
[58] Field of Search .................. 546/297; 424/263

[56] References Cited

U.S. PATENT DOCUMENTS

| | | | |
|---|---|---|---|
| 4,148,902 | 4/1979 | Rigterink | 424/266 |
| 4,160,834 | 7/1979 | Miesel | 424/250 |
| 4,275,007 | 6/1981 | Becher et al. | 424/322 |
| 4,275,077 | 6/1981 | Becher et al. | 424/322 |

OTHER PUBLICATIONS

March, Advanced Organic Chemistry, Second Edition, pp. 462–463, McGraw-Hill.

*Primary Examiner*—Alan L. Rotman
*Attorney, Agent, or Firm*—Clement J. Vicari

[57] ABSTRACT

Novel bicyclooxyheterocyclyl aroyl ureas and a process for their preparation are provided. The novel ureas are useful as the active toxicant in pesticidal compositions.

45 Claims, No Drawings

PESTICIDAL BICYCLOOXYHETEROCYCLYL AROYL UREAS

FIELD OF THE INVENTION

This invention relates in general to novel bicyclooxyheterocyclyl aroyl ureas and to a process for their preparation. In one aspect this invention relates to bicyclooxyheterocyclyl ureas which are useful as pesticides.

BACKGROUND OF THE INVENTION

Prior to the present invention, certain benzoylureas and their use as insecticides have been described in the literature. For example, U.S. Pat. Nos. 3,748,356; 3,933,908 and 3,989,842 which issued to Wellinga et al. described a series of substituted benzoylureas as having strong insecticidal activity. Wellinga et al claim compounds which are generally 1-(2,6-dihalobenzoyl) -3-(substituted phenyl) ureas with the phenyl ring being optionally substituted by halogen, lower alkyl, lower polyhaloalkyl or nitro.

A number of prior art, references discuss the insecticidal activity of the Wellinga et al compounds. For example see Van Daalen et al, *J. Agr. Food Chem.*, 21, 346 (1973), ibid, 21, 993 (1973), and Malden et al *Pestic Sci*, 4, 737 (1973).

Studies in the inhibiton of insect development by the action of 1-(4-chlorophenyl)-3-(2,6-difluorobenzoyl) urea and 1-(3,4-dichlorophenyl)-3-(2,6-dichlorobenzoyl) urea have been reported by Van Eck, *Insect Biochem.*, 9, 295 (1979), Kev, *Pestic Sci*, 9, 259 (1978) and Grosscurt, ibid, 9, 373 (1978).

Further, in the prior art U.S. Pat. Nos. 3,992,553 and 4,041,177 describe 1-(phenoxyphenyl)-3-benzoylureas as insecticides.

Several literature references describe the preparation and insecticidal use of 1-heterocyclyl-3-benzoylureas. For example see A. B. DeMilo, et al, *J. Agric. Food Chem.*, 26, 164 (1979) and K. Kramer, et al, *Environ. Ent.*, 8, 274 (1979). In general, these investigations have found that while this class of compounds do exhibit insecticidal properties, they are not as active as the 1-phenyl-3-benzoylureas found in the above references.

The patent literature has also disclosed the compositions and insectidal utility of 1-(substituted pyridyl)-3-benzoyl-ureas in U.S. Pat. No. 4,173,639 and G.B. Pat. No. 2,028,813 (to Eli Lilly), U.S. Pat. No. 4,212,870 (to Gulf Oil) and in J. Kokai 78 11,537 (to Ishihara Sangyo). 1-Pyrazinyl-3-benzoylureas have been disclosed by Eli Lilly in U.S. Pat. Nos. 4,083,977 and 4,160,834. Gulf Oil has patented 1-thiazoyl-3-benzoylureas in U.S. Pat. No. 4,164,581.

U.S. Pat. Nos. 4,148,977 and 4,160,902 discloses substituted N-(phenylaminocarbonyl) pyridine carboxylates as well as their use to control insects.

Finally, applicant's copending application Ser. No. 305,951 filed Sept. 28, 1981 discloses certain 1-(bicyclooxyphenyl)-3-benzoylureas and their use as insecticides. Prior to the present invention, however, there was no disclosure of 1-(bicyclooxyheterocyclyl)-3-aroylureas of the class hereinafter indicated.

Accordingly, one or more of the following objects will be achieved by the practice of this invention. It is an object of this invention to provide novel bicyclooxyheterocyclyl aroyl ureas. Another object of this invention is to provide certain 1-(bicyclooxyheterocyclyl)-3-aroyl ureas which exhibit insecticidal activity. A still further object is to provide novel urea compounds, such as 1-(2-[4-chloro-1-naphthoxy]-5-pyridyl)-3-(2,6-difluorobenzoyl) urea and 1-(3-bromo-2-[4-dimethylamino-5,6,7,8-tetrahydro-1-naphthoxy]-5-pyridyl)-3-2(chlorobenzoyl) urea. Another object is to provide processes for the preparation of the novel ureas. A further object is to provide novel pesticidal compositions containing the novel ureas as the active toxicant. Another object of the invention is to provide a method for controlling pests by the application of the novel pesticidal compositions. These and other objects will readily become apparent to those skilled in the art in the light of the teachings herein set forth.

SUMMARY OF THE INVENTION

In its broad aspect the invention relates to novel bicycloxyheterocyclyl aroyl ureas, pesticidal compositions containing the same, and processes for their preparation and use.

DETAILED DESCRIPTION OF THE INVENTION

The bicycloxyheterocyclyl aroyl ureas of this invention can be represented by the following generic formula:

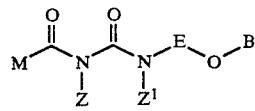

wherein M represents a monocyclic aromatic ring system or a monocyclic heterocyclic ring system containing up to two nitrogen atoms and wherein this ring can contain up to four X substituents. Each X individually can be halogen, nitro, cyano, or alkyl, polyhaloalkyl, alkoxy, polyhaloalkoxy alkylsulfenyl or polyhaloalkylsulfenyl of from one to three carbon atoms.

Z and $Z^1$ individually are hydrogen, $C_{1-8}$ alkyl, or $C_{1-8}$ alkoxy, either of which may be substituted by at least one halogen, hydroxy or alkoxy.

E is a five or six member heterocyclic ring containing up to two oxygen, sulfur or nitrogen atoms or a combination thereof. This ring may contain up to three Y substituents wherein each Y individually can be halogen, cyano or alkyl, polyhaloalkyl, alkoxy, or polyhaloalkoxy, alkyl-sulfenyl or polyhaloalkylsulfenyl of from one to three carbon atoms.

B is a bicyclic fused ring system which is attached to the oxygen through a carbocyclic ring and wherein (a) at least one ring is six-membered, unsaturated and carbocyclic and which contains the substituents R and $R^1$. (b) The second ring, herein after referred to as A, when it is not a five or six-membered saturated or unsaturated carbocyclic can be a five or six-membered saturated or unsaturated heterocyclic which can contain in any combination carbonyl or one or two oxygen or sulfur atoms and the substituents $R^2$ and $R^3$ attached to unsaturated ring carbons or the substituents $R^4$ and $R^5$ attached to saturated ring carbon atoms. Thus B may be represented by the moiety:

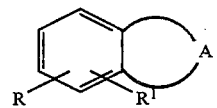

and wherein the B moiety is attached to the remainder of the molecule through the oxygen atom. Further illustrative B moieties showing the oxygen attachment to the rest of the urea molecule are as follows:

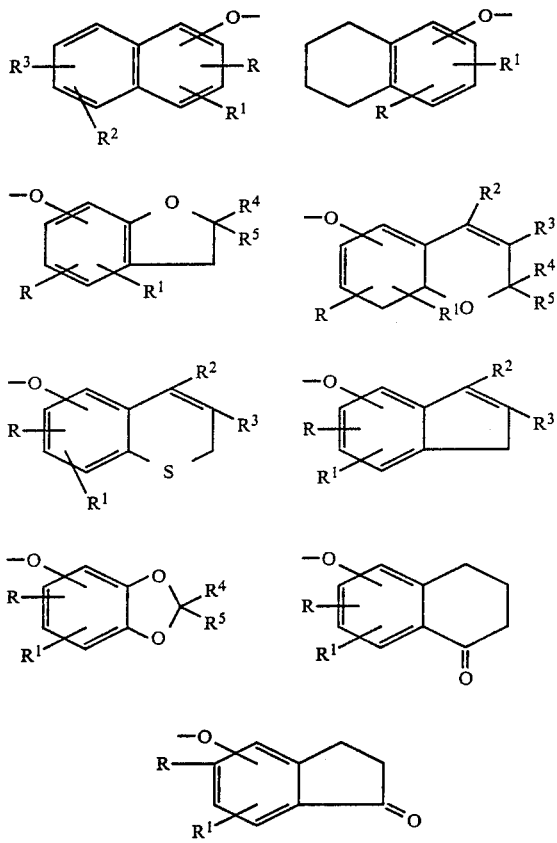

wherein R and R¹ individually may be hydrogen, halogen, nitro, cyano, amino, formamido, phenylsulfenyl, phenylsulfinyl, phenylsulfonyl, phenylsulfonate, phenylsulfamido, wherein the phenyl ring optionally may be substituted with one or more halogen, nitro, or alkyl, polyhaloalkyl, alkoxy, or polyhaloalkoxy of from one to three carbon atoms, or R and R¹ individually may be alkyl, alkoxy, polyhaloalkyl, polyhaloalkoxy, alkenyloxy, polyhaloalkenyloxy, alkynyloxy, polyhaloalkynyoxy, alkylsulfenyl, polyhaloalkylsulfenyl, alkylsulfinyl, polyhaloalkysulfinyl, alkylsulfonyl, polyhaloalkylsulfonyl, mono or di-alkylsulfamido, mono- or di-alkylaminocarbonyloxy, alkylsulfonate, polyhaloalkylsulfate of up to six carbon atoms.

R² and R³ can individually be hydrogen, halogen, nitro, cyano, or alkyl, polyhaloalkyl, alkoxy, polyhaloalkoxy, alkylthio, arylthio, alkylsulfinyl, arylsulfinyl, alkysulfonyl, arylsulfonyl, alkylsulfamido, arylsulfamido, alkoxycarbonylamino or alkylcarbonylamino of from one to eight carbon atoms.

R⁴ and R⁵ individually can be alkyl or polyhaloalkyl of from one to six carbon atoms.

A preferred class of aroyl ureas coming within the above generic formula can be represented by:

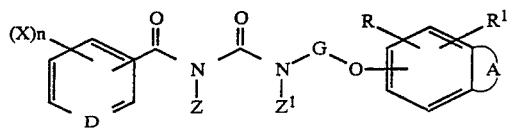

wherein D is nitrogen or carbon, G is a six-membered heterocyclic ring containing one or two nitrogen atoms and up to three y substitutents, n has a value of zero to four and R, R¹, X, Y, Z, Z¹ and A are as previously described.

Particularly preferred compositions of this invention are those in which the G moiety is a pyridine ring and the B moiety is a bicyclic fused ring system which can be attached to the linking oxygen atom through a carbocyclic ring. Thus these compositions can be conveniently represented by the following formula:

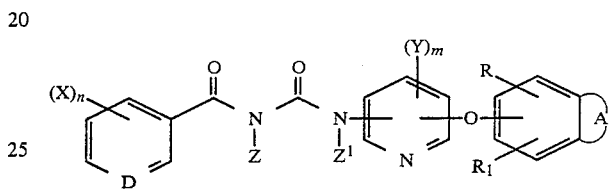

wherein m is zero to three and the other substitutents are as previously described. This invention is taken to include the N-oxide and addition salt complexes of the pyridine moieties.

The most preferred compounds of this invention are those in which the pyridine ring is substituted at the two positions by the oxygen and at the five position by the nitrogen of the urea. This is illustrated by formula 1.

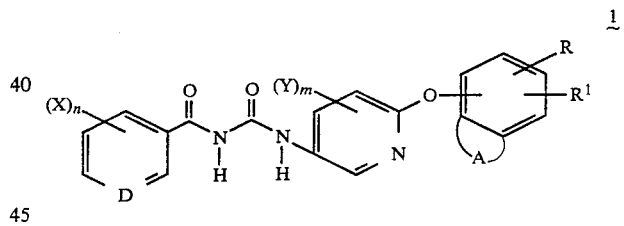

Wherein the substitutents are as previously indicated.

Illustrative compounds which can be prepared in accordance with the teachings of this invention include, but are not limited to, the following:

1-(2-[4-chloro-1-naphthoxy]-5-pyridyl)-3-(2,6-difluoro benzoyl)urea, 1-(2-[4-chloro-1-naphthoxy]-5-pyridyl)-3-(2-chloro-6-fluorobenzoyl) urea, 1-(3-chloro-2-[4-chloro-5,6,7,8-tetrahydro-1-naphthoxy]-5-pyridyl)-3-(2,6-difluorobenzoyl urea, 1-(3-chloro-2-[4-chloro-5,6,7,8-tetrahydro-1-naphthoxy]-5-pyridyl)-3-(2-chloro-6-fluorobenzoyl) urea, 1-(3-chloro-2-[4-chloro-1-naphthoxy]-5-pyridyl)-3-(2,6-difluorobenzoyl) urea, 1-(3-chloro-2-[4-chloro-1-naphthoxy]-5-pyridyl)-3-(2-chloro-6-fluorobenzoyl urea, 1-(2-[4-chloro-1-naphthoxy]-3-methyl-5-pyridyl)-3-(2,6-difluorobenzoyl) urea, 1-(2-[4-chloro-1-naphthoxy]-3-methyl-5-pyridyl)-3-(2-chloro-6-fluorobenzoyl) urea, 1-(3-chloro-2-[1,6-dibromo-2-naphthoxy]-5-pyridyl)-3-(2,6-difluorobenzoyl) urea, 1-(3-chloro-2-[1,6-dibromo-2-naphthoxy]-5-pyridyl)-3-(2-chloro-6-fluorobenzoyl) urea, 1-(3-chloro-2-[4-methoxy-1-naphthoxy]-5-pyridyl)-3-(2,6-difluorobenzoyl) urea, 1-(3-methoxy-2-[4-methoxy-1-naphthoxy]-5-pyridyl)-3-(2,6-difluorobenzoyl) urea, 1-(3-bromo-2-[4-dimethylamino-5,6,7,8-tetrahydro-1-naphthoxy]-5-pyridyl)-3-(2,6-difluorobenzoyl) urea, 1-(3-bromo-2-[4-dimethylamino-5,6,7,8-tetrahydro-1-naphthoxy]-5-pyridyl)-3-(2-chlorobenzoyl) urea, 1-(3-chloro-2-[4-dimethylamino-5,6,7,8-tetrahydro-1-naphthoxy]-5-pyridyl)-3-(2-chlorobenzoyl) urea, 1-(3-chloro-2-[4-dimethylamino-5,6,7,8-tetrahydro-1-naphthoxy]-5-pyridyl)-3-(2,6-difluorobenzoyl) urea, 1-(2-[4-dimethylamino-5,6,7,8-tetrahydro-1-naphthoxy]-3-methyl-5-pyridyl)-3-(2-chloro-6-fluorobenzoyl) urea, 1-(2-[4-dimethylamino-5,6,7,8-tetrahydro-1-naphthoxy]-3-methyl-5-pyridyl)-3-(2-chlorobenzoyl) urea, and the like.

It is accordingly, readily apparent from the scope of the preceding formulae that this invention encompasses a wide variety of novel ureas. Table A-M which follow, set forth preferred sub classes within the broad generic formula and illustrates specific compounds galling within the particular classes.

TABLE A
Pesticidal Bicyclooxyheterocyclyl Aroyl Ureas

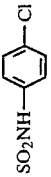

| X | X¹ | X² | X³ | Y | Y¹ | Y² | Z | Z¹ | R | R¹ | R² | R³ |
|---|---|---|---|---|---|---|---|---|---|---|---|---|
| F | F | H | H | H | H | H | H | H | Cl | Cl | H | H |
| OCH₃ | Cl | H | H | H | H | H | H | H | Cl | Cl | H | H |
| Cl | Cl | H | H | Cl | H | H | H | H | Cl | Cl | H | H |
| Cl | F | H | H | Br | H | H | H | H | Cl | Cl | H | H |
| OCH₃ | OCH₃ | H | H | CH₃ | H | H | H | H | Cl | Cl | H | H |
| Cl | H | H | H | Cl | H | H | H | H | Cl | H | H | H |
| Cl | H | H | H | H | H | H | CH₃ | H | Cl | H | H | H |
| OCH₃ | CH₃ | H | H | CH₃ | H | H | CH₃ | CH₃ | Cl | H | H | H |
| CH₃ | F | H | H | H | H | H | CH₃ | CH₃ | Cl | H | H | H |
| F | F | H | H | CH₃ | H | H | H | CH₃ | Cl | H | H | H |
| Cl | H | Cl | H | Cl | H | H | CH₃ | CH₃ | Cl | H | H | H |
| OC₃H₇ | F | Cl | H | CH₃ | H | H | CH₃ | CH₃ | Cl | H | H | H |
| CN | H | H | H | CH₃ | H | H | n-C₄H₇ | n-C₈H₁₇ | Cl | H | H | H |
| NO₂ | Cl | H | CH₃ | CH₃ | H | OCH₃ | H | H | OCH₃ | OCH₃ | H | H |
| Cl | F | Cl | Cl | H | H | Cl | H | H | N(CH₃)₂ | NO₂ | H | H |
| F | H | H | CH | O—i-R₃H₇ | O—i-R₃H₇ | Br | H | H | Cl | H | OCH₃ | H |
| H | H | H | H | O—i-R₃H₇ | OCH₃ | H | H | H | NO₂ | H | Cl | Cl |
| Cl | C₂H₅O | H | H | H | H | H | H | H | Br | H | H | H |
| OC₂H₅ | H | NO₂ | H | H | H | H | H | CH₂CF₃ | CN | H | H | H |
| OC₂H₅ | H | H | H | H | H | H | H | | NH₂ | | | |
| | | | | | | | | | SCH₃ | | | |
| H | H | H | OCF₃ | H | H | H | CH₃ | CH₃ |  | H | H | H |
| H | H | OC₈H₇ | H | Cl | H | H | CCl₂ | CCl₂ | SO₂CH₃ | H | H | H |
| H | O—i-C₃H₇ | H | H | Cl | H | Cl | H | H | SO₂—(4-NO₂-C₆H₄) | H | Cl | Cl |
| NO₂ | CF₃ | H | H | CH₃ | H | CH₃ | H | H | Br | SO₂NH—(4-Cl-C₆H₄) | H | H |

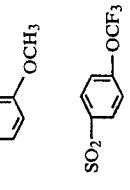

TABLE A-continued
Pesticidal Bicyclooxyheterocyclyl Aroyl Ureas
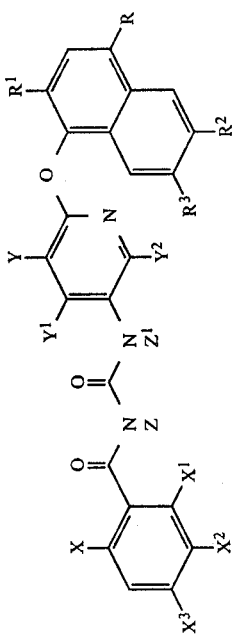
| X | X¹ | X² | X³ | Y | Y¹ | Y² | Z | Z¹ | R | R¹ | R² | R³ |
|---|----|----|----|----|----|----|---|----|---|----|----|----|
| H | H | Cl | Cl | CF₃ | H | H | H | H | S—n-hexyl | CH₃ | S—n-hexyl | H |
| CH₃ | CH₃ | H | Cl | Cl | CCl₂H | H | H | H | SCCl₃ | (CH₂)₃CH₃ | H | H |
| H | Cl | H | CH₃ | H | CH₂CHBrOCl₃ | H | H | H | SO₂i-pentyl | CH₃ | H | H |
| Cl | Cl | Cl | CH₃ | OCF₃ | H | H | H | H | N(Et)₂ | H | H | H |
| H | H | H | Cl | OCH₃ | OCH₃ | H | H | H | N(CH₃)—n-butyl | H | H | H |
| H | Cl | Cl | H | H | OCH₃ | H | H | H | N(H)—i-hexyl | H | H | H |
| H | H | H | Cl | H | | | | | N(H)—t-butyl | | | |

TABLE B
Pesticidal Bicyclooxyheterocyclyl Aroyl Ureas

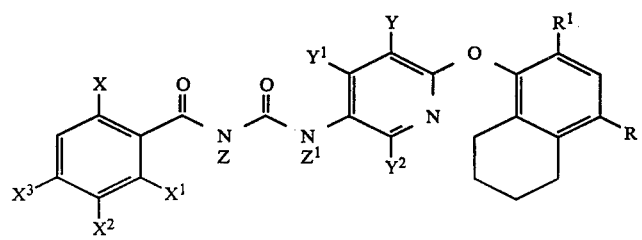

| X | X¹ | X² | X³ | Y | Y¹ | Y² | Z | Z¹ | R | R¹ |
|---|---|---|---|---|---|---|---|---|---|---|
| Cl | Cl | H | H | H | H | H | H | H | OCH₃ | H |
| F | F | H | H | H | H | H | H | H | OCH₃ | H |
| F | H | H | H | Cl | H | H | H | H | OCH₃ | H |
| CH₃ | H | H | H | Cl | H | H | H | H | OCH₃ | H |
| CH₃ | H | CH₃ | H | CH₃ | H | H | H | H | OCH₃ | H |
| CH₃ | H | H | CH₃ | CH₃ | H | H | H | H | OCH₃ | H |
| F | Cl | H | H | H | H | H | H | H | Cl | Cl |
| H | H | H | CH | H | H | H | H | H | Cl | Cl |
| H | CF₃ | H | H | Cl | H | H | H | H | Cl | Cl |
| H | H | H | OCF₃ | CH₃ | H | H | H | H Cl | Cl | |
| Cl | Cl | Cl | Cl | H | H | H | H | H | N(CH₃)₂ | H |
| Cl | Cl | H | H | H | H | H | H | H | N(CH₃)₂ | H |
| OCH₃ | OCH₃ | H | H | Cl | H | H | H | H | N(CH₃)₂ | H |
| Br | Br | H | H | Cl | H | H | H | H | N(CH₃)₂ | H |
| F | F | H | H | CH₃ | H | H | H | H | N(CH₃)₂ | H |
| F | F | F | F | CH₃ | H | H | H | H | N(CH₃)₂ | H |
| Cl | H | H. | H | H | H | H | CH₃ | CH₃ | NCHO<br>‖<br>H | H |
| Cl | Cl | H | H | CH₃ | CH₃ | H | H | H | N=CH₂—N(CH₃)₂ | H |
| Cl | H | H | Cl | Cl | H | H | CH₃ | H | Cl | NCHO |
| Cl | H | Cl | H | Cl | Cl | Cl | H | CH₃ | 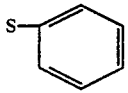 | Cl |
| Br | Br | H | H | Br | H | H | H | n-butyl | 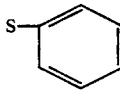 | Br |
| F | Cl | CH₃ | CH₃ | F | H | H | H | n-octyl | 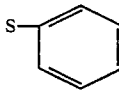 | OC₃H₂ |
| Cl | Cl | Cl | Cl | F | F | F | (CH₂)₄CH₂OH | CH₃ | 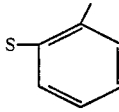 | OCCl₃ |
| Cl | H | H | H | | | | | | | |
| H | H | H | H | F | H | H | CCl₂CR₃ | H | 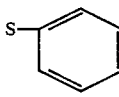 | H |
| H | F | H | F | Br | Br | Br | CH₃ | CH₃ | 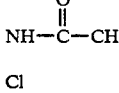 | Br |
| H | CF₃ | H | CF₃ | H | H | H | C₂H₅ | C₂H₅ | Cl | SO₂CF₃ |
| H | OCH₃ | H | OCH₃ | Cl | H | H | i-butyl | i-butyl | Cl | SO₂NHCH₃ |
| H | H | OCH₃ | OCH₃ | Cl | H | H | n-octyl | H | Br | SO₂C₄F₉ |
| H | H | H | H | CH₃ | H | H | H | H | N(CH₃)₂ | S(O)CCl₃ |
| F | F | H | H | CH₃ | H | H | H | H | OCH₃ | SOHCl₂ |
| Cl | Cl | H | H | CH₃ | H | H | H | H | H | S(O)(CH₂)₃CH₃ |
| F | Cl | H | H | H | H | H | H | H | SO₂—t-butyl | Cl |

TABLE B-continued
Pesticidal Bicyclooxyheterocyclyl Aroyl Ureas

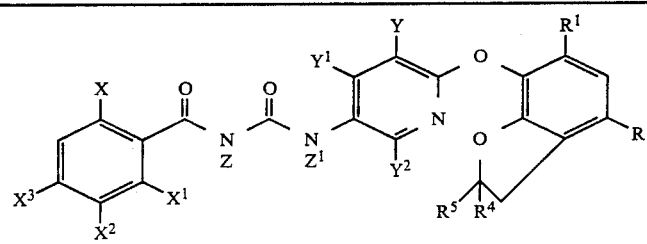

| X | $X^1$ | $X^2$ | $X^3$ | Y | $Y^1$ | $Y^2$ | Z | $Z^1$ | R | $R^1$ |
|---|---|---|---|---|---|---|---|---|---|---|
| $OCH_3$ | $OCH_3$ | H | H | H | H | H | H | H | NHC(=O)—i-butyl | Cl |
| H | H | Cl | Cl | | | | | | | |
| F | F | H | H | Cl | H | H | H | H | NHCOEt (C=O) | MHCOEt (C=O) |
| n-propyl | H | H | H | $CH_3$ | H | H | H | H | NHCO—n-hexyl (C=O) | H |
| i-propyl | i-propyl | H | H | Cl | H | Cl | H | H | OCN(H)—t-butyl (C=O) | $NME_2$ |
| H | H | H | i-propyl | Cl | H | $CH_3$ | H | H | OCN(i-propyl)$_2$ (C=O) | H |
| Cl | H | H | H | Cl | H | $CF_3$ | H | H | $OCH_2C{\equiv}CCCl_3$ | H |
| F | H | H | H | Cl | Cl | Cl | $CH_3$ | $CH_3$ | H | $OCH_2C{\equiv}CCH_4CCl_3$ |
| Cl | Cl | Cl | Cl | H | H | $CH_3$ | $CH_3$ | $CH_3$ | $SC_4Cl_9$ | H |

TABLE C
Pesticidal Bicyclooxyheterocyclyl Aroyl Ureas

| X | $X^1$ | $X^2$ | $X^3$ | Y | $Y^1$ | $Y^2$ | Z | $Z^1$ | R | $R^1$ | $R^4$ | $R^5$ |
|---|---|---|---|---|---|---|---|---|---|---|---|---|
| Cl | H | H | H | Cl | H | H | H | H | Cl | H | $CH_3$ | $CH_3$ |
| Cl | F | H | H | $CH_3$ | H | H | H | H | Cl | H | $CH_3$ | $CH_3$ |
| F | F | H | H | Br | H | H | H | H | Cl | H | $CH_3$ | $CH_3$ |
| $CH_3$ | $CH_3$ | H | H | H | H | H | H | H | Cl | H | $CH_3$ | $CH_3$ |
| $OCH_3$ | $OCH_3$ | H | H | H | H | H | H | H | Cl | H | $CH_3$ | $CH_3$ |
| F | F | H | H | $CH_3$ | H | H | H | H | Cl | H | $CH_3$ | $CH_3$ |
| Cl | Cl | H | H | Cl | H | H | H | H | Cl | Cl | $CH_3$ | $CH_3$ |
| F | Cl | H | H | Br | H | H | H | H | Cl | Cl | $CH_3$ | $CH_3$ |
| $OCH_3$ | $OCH_3$ | H | H | $CH_3$ | H | H | H | H | Cl | Cl | $CH_3$ | $CH_3$ |
| Br | Br | H | H | Cl | H | H | H | H | Cl | Cl | $CH_3$ | $CH_3$ |
| Cl | Cl | H | H | Cl | H | Cl | H | H | Cl | Cl | $CH_3$ | $CH_3$ |
| H | H | Cl | Cl | Cl | H | Cl | H | H | Cl | Cl | $CH_3$ | $CH_3$ |
| F | F | H | H | Cl | H | H | H | H | $N(CH_3)_2$ | H | $CH_3$ | $CH_3$ |
| O—i-Pr | H | H | H | Cl | H | H | H | H | $N(CH_3)_2$ | H | $CH_3$ | $CH_3$ |
| Cl | H | H | H | Cl | H | H | H | H | $N(CH_3)_2$ | H | $CH_3$ | $CH_3$ |
| H | Cl | H | Cl | H | H | H | H | H | $N(CH_3)_2$ | H | $CH_3$ | $CH_3$ |
| Cl | F | H | H | $CH_3$ | H | H | H | H | $N(CH_3)_2$ | H | $CH_3$ | $CH_3$ |
| H | H | H | $OCF_3$ | $CH_3$ | H | Cl | H | H | $N(CH_3)_2$ | H | $CH_3$ | $CH_3$ |
| F | F | H | H | Cl | H | H | H | H | H | H | $CH_3$ | H |
| Cl | H | H | H | $CH_3$ | H | Cl | H | H | H | H | n-hexyl | H |
| H | H | Cl | Cl | Cl | H | Cl | $CH_3$ | H | H | H | H | t-butyl |
| H | H | H | F | H | H | H | H | H | Cl | H | H | H |
| $CF_3$ | $CH_3$ | H | H | H | N | Cl | H | H | Cl | Cl | H | $(CH_2)_3CCl_3$ |
| $OCH_3$ | CL | H | H | H | Cl | H | H | H | H | H | $CF_3$ | $CF_3$ |

TABLE C-continued

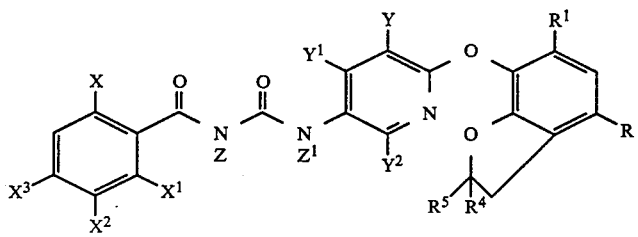

Pesticidal Bicyclooxyheterocyclyl Aroyl Ureas

| X | $X^1$ | $X^2$ | $X^3$ | Y | $Y^1$ | $Y^2$ | Z | $Z^1$ | R | $R^1$ | $R^4$ | $R^5$ |
|---|---|---|---|---|---|---|---|---|---|---|---|---|
| $OCH_3$ | F | H | H | H | H | H | H | H | H | H | H | $CF_3$ |

TABLE D

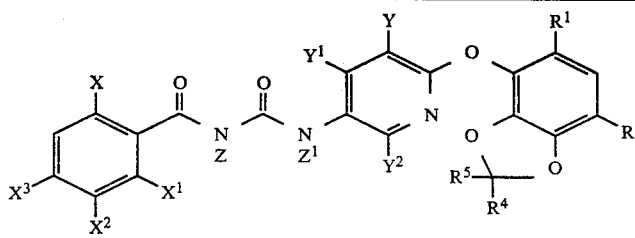

Pesticidal Bicyclooxyheterocyclyl Aroyl Ureas

| X | $X^1$ | $X^2$ | $X^3$ | Y | $Y^1$ | $Y^2$ | Z | $Z^1$ | R | $R^1$ | $R^4$ | $R^5$ |
|---|---|---|---|---|---|---|---|---|---|---|---|---|
| F | F | H | H | Cl | H | H | H | H | Cl | H | $CH_3$ | $CH_3$ |
| Cl | F | H | H | $CH_3$ | H | H | H | H | Cl | H | $CH_3$ | $CH_3$ |
| Cl | H | H | H | H | H | H | H | H | Cl | H | $CH_3$ | $CH_3$ |
| Cl | Cl | H | H | H | H | H | H | H | Cl | H | $CH_3$ | $CH_3$ |
| $OCH_3$ | $OCH_3$ | H | H | Cl | H | H | H | H | Cl | Cl | $CH_3$ | $CH_3$ |
| F | F | H | H | Cl | H | H | H | H | Cl | Cl | $CH_3$ | $CH_3$ |
| Cl | H | H | H | $CH_3$ | H | H | H | H | Cl | Cl | $CH_3$ | $CH_3$ |
| Cl | F | H | H | H | H | H | H | H | Cl | Cl | $CH_3$ | $CH_3$ |
| Cl | H | H | H | Cl | H | H | H | H | H | H | $CH_3$ | $CH_3$ |
| Cl | Cl | H | H | Cl | H | H | H | H | H | H | $CH_3$ | $CH_3$ |
| F | F | H | H | $CH_3$ | H | H | H | H | H | H | $CH_3$ | $CH_3$ |
| $OCH_3$ | $OCH_3$ | H | H | $CH_3$ | H | H | H | H | H | H | $CH_3$ | $CH_3$ |
| Cl | Cl | H | H | H | H | H | H | H | $N(CH_3)_2$ | H | $CH_3$ | $CH_3$ |
| $OCH_3$ | $OCH_3$ | H | H | Cl | H | H | H | H | $N(CH_3)_2$ | H | $CH_3$ | $CH_3$ |
| F | F | H | H | $CH_3$ | H | H | H | H | $N(CH_3)_2$ | H | $CH_3$ | H |
| Cl | H | H | H | $CH_3$ | H | H | H | H | $N(CH_3)_2$ | Cl | $CH_3$ | H |
| Cl | F | H | H | H | H | H | H | H | Cl | H | H | $CF_3$ |
| $CH_3$ | $CH_3$ | H | H | H | H | H | H | H | Cl | H | $CF_3$ | $CF_3$ |
| F | $CF_3$ | H | H | $OCF_3$ | H | H | H | H | Cl | Cl | H | t-butyl |
| $CF_3$ | $CF_3$ | H | H | H | H | $OC_3F_7$ | $CH_3$ | $CH_3$ | Cl | Cl | n-hexyl | $CH_3$ |
| H | H | $CH_3$ | $CH_3$ | H | H | H | $CH_2CH_2OH$ | H | Cl | Cl | i-Pr | $CH_2CH_3$ |
| H | H | H | H | Cl | Cl | Cl | $CH_2CH_2Cl_2$ | H | H | Cl | $CF_3$ | $C_2H_3$ |
| $CH_3$ | H | H | Cl | Br | Br | Br | H | $(CH_2)_2O(CH_2)_2CH_3$ | H | H | $C_3F_7$ | $C_3F_7$ |
| OEt | H | $NO_2$ | H | F | H | F | H | H | H | H | $CH_3$ | $(CH_2)_4CHBrCCl_3$ |

TABLE E

Pesticidal Bicyclooxyheterocyclyl Aroyl Ureas

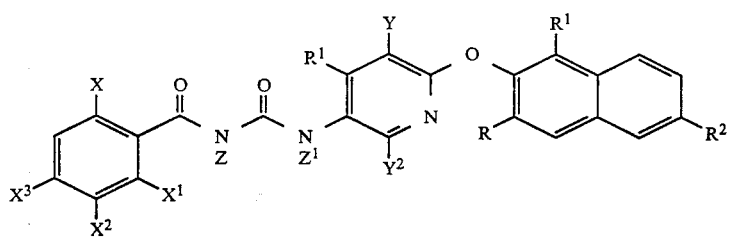

| X | $X^1$ | $X^2$ | $X^3$ | Y | $Y^1$ | $Y^2$ | Z | $Z^1$ | R | $R^1$ | $R^2$ |
|---|---|---|---|---|---|---|---|---|---|---|---|
| F | F | H | H | H | H | H | H | H | Cl | H | Cl |
| F | F | H | H | Cl | H | H | H | H | Cl | H | Cl |
| Cl | H | H | Cl | $CH_3$ | H | H | H | H | Cl | H | Cl |

TABLE E-continued
Pesticidal Bicyclooxyheterocyclyl Aroyl Ureas

| X | $X^1$ | $X^2$ | $X^3$ | Y | $Y^1$ | $Y^2$ | Z | $Z^1$ | R | $R^1$ | $R^2$ |
|---|---|---|---|---|---|---|---|---|---|---|---|
| Cl | H | H | H | $CH_3$ | H | $CH_3$ | $CH_3$ | $CH_3$ | H | H | $NO_2$ |
| $OCH_3$ | H | H | $OCH_3$ | Cl | H | Cl | $CH_3$ | $CH_3$ | H | H | $NO_2$ |
| $CH_3$ | H | H | $CH_3$ | H | Cl | Cl | H | H | H | H | $NO_2$ |
| F | F | F | F | H | $CH_3$ | H | H | H | H | CN | $NO_2$ |
| H | H | H | H | H | H | H | H | H | H | H | $O(CH_2)_5CH_3$ |
| H | H | Cl | H | Cl | H | H | $CH_3$ | H | H | H | S—n-hexyl |
| H | H | Cl | Cl | Cl | H | H | H | H | H | H | $S(O)C_4Cl_9$ |
| $OCH_3$ | H | Cl | H | $CH_3$ | $CH_3$ | $CH_3$ | H | $CH_3$ | H | H | $SO_2(CH_2)_4CHBrCCl_3$ |
| F | Cl | H | H | Cl | Cl | Cl | H | H | Cl | Cl | $O(CH_2)_4CHBrCCl_3$ |
| H | Cl | H | H | H | H | H | H | H | H | H | $SO_2N(CH_3)_2$ |
| Br | Br | H | H | H | H | H | H | H | Br | H | S(O)—t-butyl |
| H | H | H | Br | Cl | H | H | H | H | Cl | Cl | NHC(O)—i-hexyl |
| H | Cl | H | Cl | Br | H | H | H | H | H | Cl | S—n-butyl |
| F | F | H | F | Br | H | ·Br | H | H | $NO_2$ | H | $SO_2$-(3,4-dichlorophenyl) |
| H | F | H | H | H | H | Br | H | H | H | H | S(O)-(2,4-dimethylphenyl) |

TABLE F

| X | $X^1$ | Y | R | $R^1$ |
|---|---|---|---|---|
| F | F | H | H | H |
| Cl | F | H | H | Cl |
| Cl | H | H | H | $N(CH_3)_2$ |
| Cl | Cl | Cl | H | H |
| $OCH_3$ | $OCH_3$ | Cl | H | Cl |
| $CH_3$ | $CH_3$ | $CH_3$ | H | Cl |
| Cl | Cl | $CH_3$ | Cl | Cl |
| F | F | Br | Cl | $N(CH_3)_2$ |

TABLE G

| X | $X^1$ | Y | R | $R^1$ |
|---|---|---|---|---|
| F | F | Cl | Cl | Cl |
| F | Cl | H | H | Cl |
| Cl | H | Cl | H | Cl |
| H | $OCH_3$ | Cl | H | H |
| $OCH_3$ | $OCH_3$ | $CH_3$ | H | H |
| $CH_3$ | $CH_3$ | Cl | H | $N(CH_3)_2$ |

TABLE H

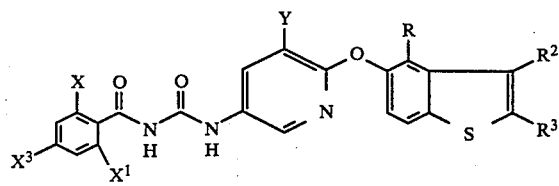

| X | X¹ | X² | Y | R | R² | R³ |
|---|---|---|---|---|---|---|
| F | F | H | Cl | H | H | H |
| Cl | F | H | H | Cl | H | H |
| Cl | Cl | H | CH₃ | Br | H | H |
| H | Cl | Cl | CF₃ | NO₂ | H | H |
| CH₃ | CH₃ | CH₃ | OCH₃ | H | H | H |
| Cl | H | H | Cl | Cl | H | H |
| H | H | OCH₃ | OCH₃ | Cl | Cl | Cl |
| Cl | F | H | Br | Cl | H | H |
| F | F | H | CH₃ | Cl | H | H |
| Cl | F | H | CH₃ | H | H | H |

TABLE I

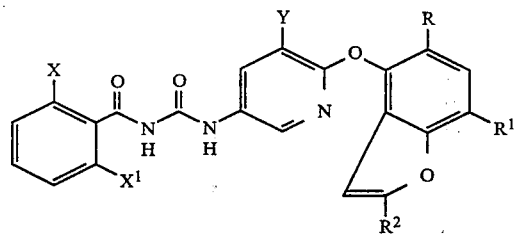

| X | X¹ | Y | R | R¹ | R² |
|---|---|---|---|---|---|
| H | Cl | Cl | H | Cl | H |
| Cl | Cl | H | H | Cl | H |
| Cl | F | CH₃ | H | H | H |
| CH₃ | Cl | Cl | H | N(CH₃)₂ | H |
| Cl | NO₂ | Cl | H | Cl | CH₃ |
| CH₃ | CH₃ | CH₃ | H | Cl | Cl |
| F | F | H | Cl | Cl | H |
| Cl | F | H | Cl | Cl | H |
| F | F | Cl | Cl | N(CH₃)₂ | CH₃ |

TABLE J

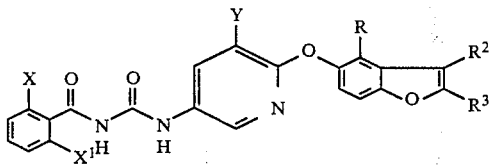

| X | X¹ | Y | R | R² | R³ |
|---|---|---|---|---|---|
| F | F | Cl | H | H | CH₃ |
| H | Cl | Cl | H | H | H |
| Cl | F | CH₃ | Cl | H | Cl |
| OCH₃ | OCH₃ | CH₃ | Cl | Cl | Cl |
| CH₃ | CH₃ | H | H | H | H |
| Cl | Cl | H | Cl | H | Cl |

TABLE K

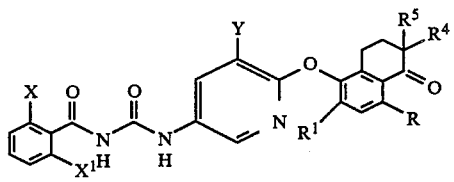

| X | X¹ | Y | R | R¹ | R⁴ | R⁵ |
|---|---|---|---|---|---|---|
| F | F | CH₃ | H | H | H | H |
| Cl | F | Cl | Cl | H | H | H |
| Cl | H | H | Cl | Cl | H | H |
| H | OCH₃ | Cl | H | H | CH₃ | CH₃ |
| Cl | Cl | H | Cl | H | CH₃ | CH₃ |
| F | F | CH₃ | Cl | Cl | CH₃ | CH₃ |

TABLE L

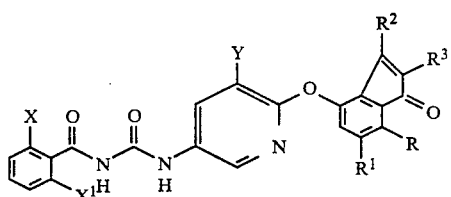

| X | X¹ | Y | R | R¹ | R² | R³ |
|---|---|---|---|---|---|---|
| F | F | Cl | H | H | H | H |
| OCH₃ | OCH₃ | CH₃ | Cl | H | H | H |
| OCF₃ | H | Br | Cl | Cl | H | H |
| F | H | H | H | Cl | H | H |
| F | Br | F | H | H | OCH₃ | H |
| F | NO₂ | OCH₃ | H | H | H | CH₃ |
| CN | H | CF₃ | H | H | OEt | CH₃ |
| Br | Br | Br | Cl | Cl | OCH₃ | CF₃ |

TABLE M

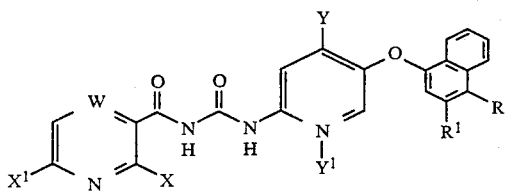

| W | X | X¹ | Y | Y¹ | R | R¹ |
|---|---|---|---|---|---|---|
| CH | Cl | H | Cl | H | H | H |
| CH | Cl | Cl | Cl | Cl | Cl | Cl |
| CH | OCH₃ | H | CH₃ | H | Cl | H |
| CF | F | H | CH₃ | H | H | H |
| CCl | H | H | H | H | Cl | H |
| CCl | H | Cl | Cl | H | H | H |
| CCl | F | H | CH₃ | H | Cl | H |
| CCl | Cl | Cl | CH₃ | H | H | H |
| N | Cl | H | | | OCH₃ | OCH₃ |
| N | OCH₃ | H | Cl | Cl | Cl | CL |
| N | CF₃ | H | Cl | Cl | H | H |
| N | CH₃ | Cl | Br | CH₃ | Cl | NO₂ |
| N | Br | OCH₃ | CH₃ | CH₃ | Br | OCH₃ |

The ureas of formula 1 can be conveniently prepared through the reaction of an amine 3 with an aroylisocyanate 2 according to the reaction scheme I.

Scheme I

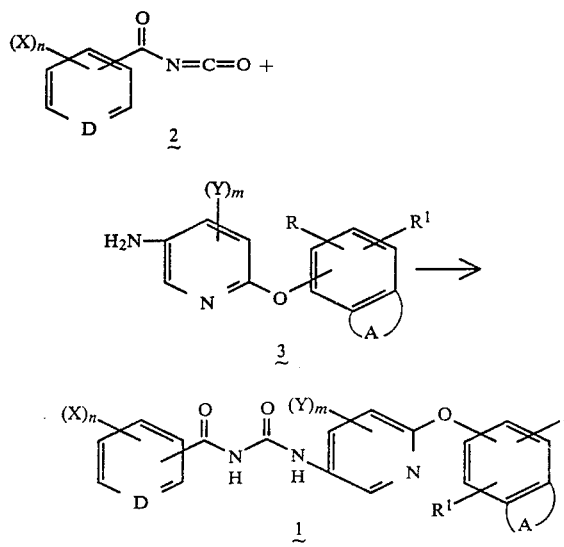

Alternatively, the compositions of structure 1 may be prepared through the reaction of a heterocyclylisocyanate 4 with a benzamide 5 according to the reaction scheme II.

Scheme II

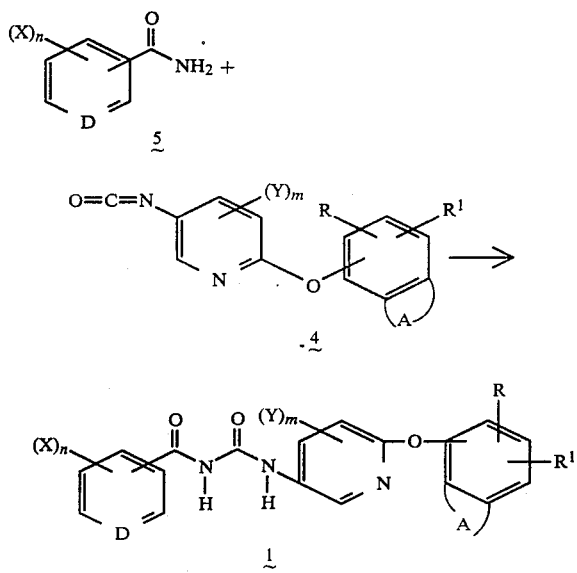

The reactions described in Schemes I and II generally proceed without the addition of other reagents. However, the use of a inert solvent is desirable. Suitable solvents include halogenated hydrocarbon and aromatic hydrocarbons.

The intermediates shown in Schemes I and II for the preparation of compositions of this invention can be prepared according to generally accepted proceedures. Thus, the substituted aroyl isocyanates 2 are prepared from the substituted benzamides 5 following the general procedure of Speziale et al., *J. Org. Chem.*, 27, 3742 (1962).

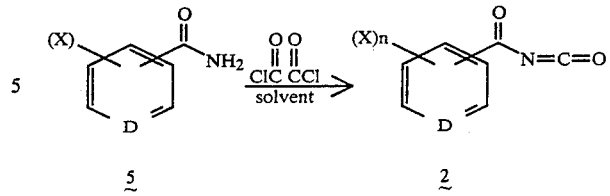

The benzamides 5 are either available commercially or can be prepared according to customary processes.

The heterocyclic amines 3 can be prepared according to the two step sequence illustrated below.

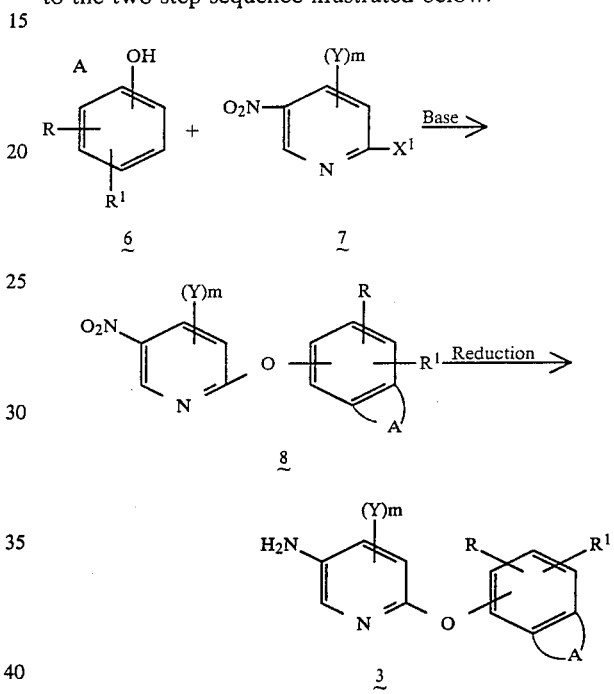

wherein $X^1$ is halogen and the other substitutents are as previously described.

The reaction of the bicyclic phenol 6 with the 2-halo-5-nitro pyridine derivative 7 proceeds in the presence of a base in an inert solvent at an elevated temperature to afford the nitro ether 8. Suitable bases include sodium hydride, sodium or potassium hydroxide or sodium or potassium carbonate. Suitable solvents include aromatic hydrocarbons such as toluene or xylene, dialkyl ketones such as methyl ethyl ketone, acetone or isobutyl methyl ketone, or other inert solvents such as dimethyl formamide or dimethyl sulfoxide. If the reaction is heterogeneous a phase-transfer agent such as a quarternary ammonium halide or a crown ether may be added.

The reduction of the nitro ether 8 to the heterocyclic amine 3 can be accomplished under a hydrogen atmosphere using a heterogeneous hydrogenation catalyst. Such a catalysts include platinum or palladium on an inert support or a Raney nickel catalyst. In general these reductions can be performed under a wide range of temperatures and pressures. However, it is preferable to use a pressure range at 80–120 psi at ambient temperature. The solvents of choice include aromatic hydrocarbons, such as toluene or alcohols such as ethanol. Alternatively, this reduction may also be accomplished by a chemical reductant such as a transition metal or its salts in a mineral acid solution. In general tin or iron and their salts in hydrochloric acid are preferred. A co-solvent such as dioxane or alcohols may be added to improved the reactant solubility in the reaction medium.

The amine 3 can be converted to the isocyanate 4 by the reaction of phosgene employing generally accepted procedures.

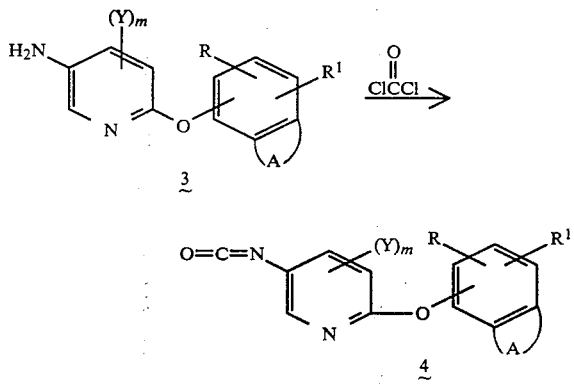

Both the bicyclic phenols 6 and the 2-halo-5-nitro pyridines 7 are available commercially or may be prepared by well known methods from the chemical literature.

Illustrative nitro compounds which are useful as starting materials were prepared in accordance with the procedure of Example 1, Part A, and include, but are not limited to:
2-(4-Chloro-1-naphthoxy)-3-bromo-5-nitropyridine,
2-(1,6-Dibromo-2-naphthoxy)-3-bromo-5-nitropyridine,
2-(4-chloro-1-naphthoxy)-3-chloro-5-nitropyridine,
2-(1,6-Dibromo-2-naphthoxy)-3-chloro-5-nitropyridine,
2-(4-methoxy-1-naphthoxy)-3-chloro-5-nitropyridine
2-(4-methoxy-1-naphthoxy)-5-nitropyridine
2-(1-naphthoxy)-3-chloro-5-nitropyridine
2-(1-naphthoxy)--5-nitropyridine,
2-(4-chloro-1-naphthoxy)-3-methyl-5-nitropyridine,
2-(4-methoxy-1-naphthoxy)-3-methyl-5-nitropyridine
2-(1-naphthoxy)-3-methyl-5-nitropyridine,
2-(5,6,7,8-tetrahydro-1-naphthoxy)-5-nitropyridine,
2-(4-chloro-5,6,7,8-tetrahydro-1-naphthoxy)-3-chloro-5-nitropyridine,
2-(2,2-Dimethyl-2,3-dihydro-7-benzofuranoxy)-3-bromo-5-nitropyridine,
2-(4-chloro-5,6,7,8-tetrahydro-1-naphthoxy)-3-methyl-5-nitropyridine,
2-(4-Dimethylamino-5,6,7,8-tetrahydro-1-naphthoxy)-3-bromo-5-nitropyridine,
2-(4-Dimethylamino-5,6,7,8-tetrahydro-1-naphthoxy)-3-methyl-5-nitropyridine,
2-(4-Dimethylamino-5,6,7,8-tetrahydro-1-naphthoxy)-3-chloro-5-nitropyridine, and the like.

Amine compounds 3 prepared in accordance with Example 1, Part B include:
2-(4-Dimethylamino-5,6,7,8-tetrahydro-1-naphthoxy)-3-methyl-5-aminopyridine,
2-(4-Dimethylamino-5,6,7,8-tetrahydro-1-naphthoxy)-3-chloro-5-aminopyridine, and the like.

In accordance with the procedure of Example 2, Part A, the following amine starting materials were also prepared:
2-(2,2-Dimethyl-2,3-dihydro-7-benzofuranoxy)-3-bromo-5-amino-pyridine,
2-(1,6-Dibromo-2-naphthoxy)-3-bromo-5-aminopyridine,
2-(4-chloro-1-naphthoxy)-3-bromo-5-aminopyridine,
2-(4-chloro-1-naphthoxy)-3-chloro-5-aminopyridine,
2-(1,6-Dibromo-2-naphthoxy)-3-chloro-5-aminopyridine,
2-(4-methoxy-1-naphthoxy)-3-chloro-5-aminopyridine,
2-(4-methoxy-1-naphthoxy)-5-aminopyridine
2-(4-chloro-1-naphthoxy)-3-methyl-5-aminopyridine,
2-(1-naphthoxy)-3-chloro-5-aminopyridine,
2-(1-naphthoxy)-3-methyl-5-aminopyridine,
2-(4-methoxy-1-naphthoxy)-3-methyl-5-aminopyridine,
2-(5,6,7,8-tetrahydro-1-naphthoxy)-5-aminopyridine
2-(4-chloro-5,6,7,8-tetrahydro-1-naphthoxy)-3-chloro-5-aminopyridine,
2-(4-chloro-5,6,7,8-tetrahydro-1-naphthoxy)-3-methyl-5-aminopyridine and
2-(4-Dimethylamino-5,6,7,8-tetrahydro-1-naphthoxy)-3-bromo-5-aminopyridine.

The bicyclooxyheterocyclyl-3-aroylureas are, with varying degrees of efficiency, useful in combating insect pests. The insecticidal activity of the compounds prepared according to this invention is summarized in Table V. In addition selected compounds have exhibited miticidal activity. This is shown in Table VI.

The compounds contemplated in this invention may be applied as insecticides and miticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, o nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex either alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, or instance, phytotoxicity, to the toxicants. The toxicants are so chemically inert that they are not compatible with substantially any other constituents of the spray schedule, and they may be used in the soil, upon the seeds, or the roots of plants without injuring either the seeds or roots of plants.

The following examples illustrate the best mode presently contemplated for the practice of this invention.

EXAMPLE I

Preparation of
1-(2-[Naphthoxy]-5-pyridyl)-3-(2,6-difluorobenzoyl) urea

Part A: Preparation of 2-(1-Naphthoxy)-5-Nitropyridine

To a solution of 17.0 g. (0.107 mol.) of 2-chloro-5-nitro pyridine in 250 ml of DMF was added 15.4 g. (0.112 mol.) of potassium carbonate and 15.5 g. (0.107 mol.) of 1-naphthol. The resulting mixture was heated up to 125° C. for 3 hours. Additional potassium carbonate (1.5 g., 0.011 mol.) was added. This mixture was continued heating for 7 hours, cooled, and concentrated to give a black gummy product. It was then dissolved in 200 ml. of ethyl acetate. Florisil (60–100 mesh, 40 g.) was added to the above solution and the resulting mixture was concentrated to give brown powder. This material was packed on top of a column (450 g. florisil in hexane). Elution with hexane/ethyl acetate (96:4) gave 14.3 g. (0.054 mol., 50.3% of bright yellow crystals; mp. 87.3°–89.3° C.

Part B: Preparation of 2-(1-naphthoxy)-5-aminopyridine

To a solution of 13.11 g. (0.049 mol.) of 2-(1-naphthoxy)-5-nitropyridine in 250 ml. of toluene was added 1.31 g. of 5% palladium in carbon. The resulting mixture was placed in a 500 ml. Rocking Parr pressure vessel under 100 psig of hydrogen at r.t. for 3 hours. The mixture was filtered through celite and the filtrate was concentrated to give 11.5 g. (0.048 mol., 99.4%) of a yellow solid; mp. 82.2°–83.7°

Part C: Preparation of 1-(2-[1-Naphthoxy]-5-pyridyl-3-(2,6-difluorobenzoyl) urea A mixture of 2.5 g. of 2-(1-naphthoxy)-5-amino pyridine and 8.13 ml. of toluene was heated up to 50° C. To this resulting homgeneous solution was added a solution of 3.1 g. of 2,6-difluorobenzoyl isocyanate in 2 ml. of toluene. The resulting mixture was heated at 80° for 1.5 hours, cooled, and filtered to give 4.7 g. of white crystals; mp. 223.5°–224.0°.

EXAMPLE 2

Preparation of
1-(2-[4-Chloro-5,6,7,8-tetrahydro-1-naphthoxy]-3 chloro-5-pyridyl)-3(2-chloro-6-fluorobenzoyl) urea

Part A: Preparation of 2-(4-Chloro-5,6,7,8-tetrahydro-1-naphthoxy)-3-chloro-5-amino pyridine To a solution of 2.64 g. (11.7 mmol.) of stannous chloride in 2.4 ml. of concentrated hydrochloric acid and 1.75 ml. of p-dioxane at 50° was added 1.2 g. (3.54 mmol.) of 2-(4-chloro-5,6,7,8-tetrahydro-1-naphthoxy)-3-chloro-5-nitropyridine. The resulting mixture was heated up to reflux for 0.5 hours, cooled, and poured into sodium hydroxide (pH 14) in cracked ice. This mixture was extracted twice with 150 ml. of methylene chloride. The combined organic layer was washed with water and brine. It was then dried ($Na_2SO_4$) and concentrated to give 1.0 g. (3.23 mmole) of light purple solid; mp. 129.8°–132.3°

Part B: Preparation of 1-(2-[4-chloro-5,6,7,8-tetra-hydro-1-naphthoxy]-3-chloro-5-pyridyl)-3-(2-chloro-6-fluorobenzoyl) urea A mixture of 0.5 g. of 2-(4-chloro-5,6,7,8-tetrahydro-1-naphthoxy)-3-chloro-5-aminopyridine and 5 ml. of toluene was heated up to 50°. To this resulting solution was added 0.52 g. of 2-chloro-6-fluorobenzoyl isocyanate in 6 ml. of toluene. The mixture was heated at 80° for 1.5 hours, cooled, and filtered to give 0.7 g. of white crystals; mp. 243.5°–244.5°.

EXAMPLES 3–53

In a manner similar to that employed in the preceding examples, and using one of the synthesis schemes previously disclosed, other urea compounds were prepared. The indentity of the substituents on the generic formula, analytical data, and other physical properties are set forth below in Tables I–IV.

TABLE I

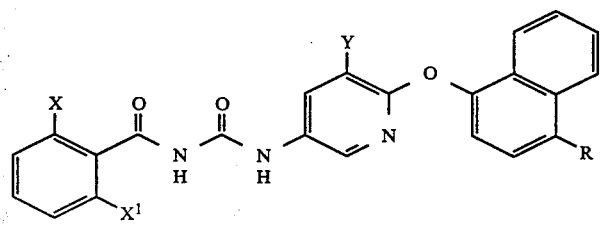

Physical Properties of 1-(2-[1-Naphthoxy]-5-pyridyl)-3-benzoylureas

| Example | MP °C. | Mol. Formula | X | $X^1$ | Y | R | Calculated C | Calculated H | Calculated N | Found C | Found H | Found N |
|---|---|---|---|---|---|---|---|---|---|---|---|---|
| 1 | 223.5–224 | $C_{23}H_{15}F_2N_3O_3$ | F | F | H | H | 65.87 | 3.61 | 10.02 | 65.77 | 3.53 | 9.96 |
| 3 | 210.5–212.5 | $C_{23}H_{13}BrCl_2FN_3O_3$ | Cl | F | Br | Cl | 50.30 | 2.38 | 7.65 | 52.10 | 2.38 | 7.75 |
| 4 | 240–242 | $C_{23}H_{13}BrClF_2N_3O_3$ | F | F | Br | Cl | 51.95 | 2.27 | 7.90 | 50.43 | 2.33 | 7.47 |
| 5 | 256–257 | $C_{23}H_{13}BrCl_3N_3O_3$ | Cl | Cl | Br | Cl | 48.84 | 2.32 | 7.43 | 51/51 | 7.64 | 6.85 |
| 6 | 239–240 | $C_{23}H_{14}BrCl_2N_3O_3$ | Cl | H | Br | Cl | 52.01 | 2.66 | 7.91 | 51.57 | 2.49 | 1.78 |
| 7 | 250–251 | $C_{23}H_{13}Cl_4N_3O_3$ | Cl | Cl | Cl | Cl |  | 52.9681[1] |  |  | 520.9681[1] |  |
| 8 | 235–237 | $C_{23}H_{14}Cl_3N_3O_3$ | Cl | H | Cl | Cl | 56.76 | 2.90 | 8.63 | 56.32 | 2.73 | 8.57 |
| 9 | 227–235 | $C_{26}H_{22}ClN_3O_6$ | $OCH_3$ | $OCH_3$ | Cl | $OCH_3$ | 61.48 | 4.37 | 8.27 | 61.01 | 4.37 | 8.31 |
| 10 | 187–189 | $C_{24}H_{16}ClF_2N_3O_4$ | F | F | Cl | $OCH_3$ |  | 483.0797[1] |  |  | 483.0767[1] |  |
| 11 | 218–219 | $C_{24}H_{17}Cl_2N_3O_4$ | Cl | H | Cl | $OCH_3$ | 59.77 | 3.55 | 8.71 | 59.82 | 3.46 | 8.67 |
| 12 | 227–229 | $C_{23}H_{14}ClF_2N_3O_3$ | F | F | Cl | H |  | 453.0697[1] |  |  | 453.0697[1] |  |
| 13 | 242–244 | $C_{23}H_{14}Cl_2FN_3O_3$ | Cl | F | Cl | H | 58.74 | 3.00 | 8.94 | 58.63 | 2.95 | 8.49 |
| 14 | 209–211 | $C_{24}H_{17}ClFN_3O_3$ | Cl | F | $CH_3$ | H | 64.07 | 3.81 | 9.34 | 63.62 | 3.67 | 8.31 |
| 15 | 207.5–209.5 | $C_{24}H_{17}F_2N_3O_3$ | F | F | $CH_3$ | H | 66.30 | 3.95 | 9.70 | 66.18 | 3.90 | 9.54 |
| 16 | 211.5–212.5 | $C_{25}H_{17}ClFN_3O_4$ | F | Cl | $CH_3$ | $OCH_3$ | 62.57 | 3.99 | 8.76 | 63.96 | 9.51 | 8.16 |
| 17 | 180.54–183.5 | $C_{25}H_{19}F_2N_3O_4$ | F | F | $CH_3$ | $OCH_3$ | 64.88 | 4.13 | 9.07 | 65.17 | 4.22 | 8.86 |
| 18 | 217–219 | $C_{24}H_{16}ClF_2N_3O_3$ | F | F | $CH_3$ | Cl |  | 467.0848[1] |  |  | 467.0854[1] |  |
| 19 | 233–235 | $C_{24}H_{16}Cl_2FN_3O_3$ | F | Cl | $CH_3$ | Cl |  | 483.0553[1] |  |  | 483.0534[1] |  |
| 20 | 209.5–211.5 | $C_{24}H_{17}F_2N_3O_4$ | F | F | H | $OCH_3$ | 64.14 | 3.81 | 9.35 | 63.85 | 3.70 | 9.75 |
| 21 | 193.2–195.2 | $C_{24}H_{17}ClFN_3O_4$ | F | Cl | H | $OCH_3$ | 61.88 | 3.68 | 9.02 | 61.85 | 3.63 | 8.69 |
| 22 | 182.5–183.5 | $C_{24}H_{18}ClN_3O_4$ | H | Cl | H | $OCH_3$ | 64.36 | 4.05 | 9.38 | 64.20 | 3.90 | 9.34 |
| 23 | 239–240 | $C_{23}H_{13}Cl_3FN_3O_4$ | Cl | F | Cl | Cl | 54.73 | 2.60 | 8.33 | 54.87 | 2.45 | 8.11 |
| 24 | 200 dec | $C_{23}H_{14}Cl_2FN_3O$ | F | Cl | H | H | 58.74 | 3.00 | 8.94 | 58.11 | 2.85 | 8.72 |
| 25 | 191.0–192.0 | $C_{23}H_{15}ClFN_3O_3$ | F | F | Cl | Cl | 63.39 | 3.47 | 9.64 | 62.96 | 3.32 | 9.58 |
| 26. | 199 dec | $C_{23}H_{14}ClF_2N_3O_3$ | F | F | H | Cl | 60.7 | 3.11 | 9.26 | 60.95 | 3.12 | 9.29 |
| 27. | 200 dec | $C_{23}H_{14}Cl_2FN_3O_3$ | Cl | F | H | Cl | 58.74 | 3.00 | 8.94 | 58.11 | 2.85 | 8.72 |

[1] Exact molecular weight measurement by mass spectrum peak matching technique

TABLE II

Physical Properties of 1-(2-[2-Naphthoxy]-5-pyridyl)-3-benzoylureas

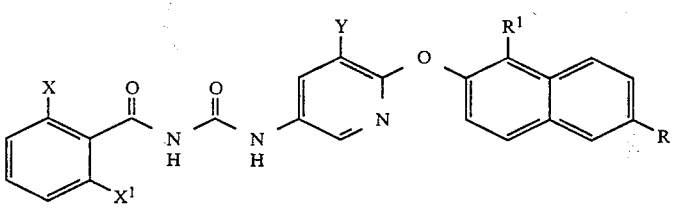

| Example | MP °C. | Mol. Formula | X | $X^1$ | Y | R | $R^1$ | Calculated C | Calculated H | Calculated N | Found C | Found H | Found N |
|---|---|---|---|---|---|---|---|---|---|---|---|---|---|
| 28 | 283° dec | $C_{23}H_{12}Br_3ClFN_3O_3$ | Cl | F | Br | Br | Br | 41.08 | 1.80 | 6.25 | 41.02 | 1.72 | 6.15 |
| 29 | 270° dec | $C_{23}H_{12}Br_3F_2N_3O_3$ | F | F | Br | Br | Br | 42.11 | 1.84 | 6.41 | 41.91 | 1.66 | 6.34 |
| 30 | 283° dec | $C_{23}H_{12}Br_3Cl_2N_3O_3$ | Cl | Cl | Br | Br | Br | 40.10 | 1.76 | 6.10 | 40.38 | 1.78 | 6.04 |
| 31 | 239.5–241.5 | $C_{23}H_{13}Br_3ClN_3O_3$ | Cl | H | Br | Br | Br | 42.20 | 2.00 | 6.42 | 42.93 | 2.00 | 6.52 |
| 32 | 300° dec | $C_{23}H_{12}Br_2Cl_2FN_3O_3$ | Cl | F | Cl | Br | Br | 43.98 | 1.93 | 6.69 | 43.53 | 1.82 | 6.60 |
| 33 | 280° dec | $C_{23}H_{12}Br_2ClF_2N_3O_3$ | F | F | Cl | Br | Br | 45.17 | 1.98 | 6.87 | 44.87 | 1.91 | 6.78 |
| 34 | 244° dec | $C_{23}H_{12}Br_2Cl_3N_3O_3$ | Cl | Cl | Cl | Br | Br | 42.86 | 1.88 | 6.52 | 43.01 | 1.87 | 6.54 |
| 35 | 243–246° | $C_{23}H_{13}Br_2Cl_2N_3O_3$ | Cl | H | Cl | Br | Br | 45.28 | 2.15 | 6.89 | 45.31 | 2.08 | 6.84 |

TABLE III

Physical Properties of 1-(2-[5,6,7,8-Tetrahydro-1-nyphthoxy]-5-pyridyl)-3-benzoylureas

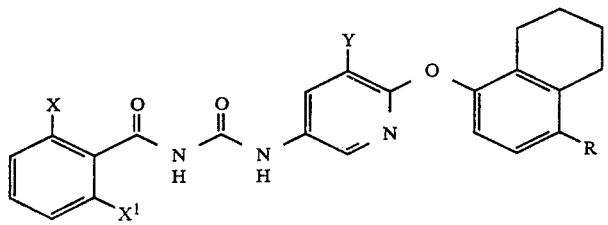

| | | | | | | | Elemental Analysis | | | | | |
|---|---|---|---|---|---|---|---|---|---|---|---|---|
| | | | | | | | Calculated | | | Found | | |
| Example | MP °C. | Mol. Formula | X | X[1] | Y | R | C | H | N | C | H | N |
| 2 | 243.5–244.5 | $C_{23}H_{17}Cl_3FN_3O_3$ | Cl | F | Cl | Cl | 54.30 | 3.37 | 8.26 | 54.15 | 3.63 | 7.78 |
| 36 | 193.5–195.0 | $C_{23}H_{20}ClN_3O_3$ | Cl | H | H | H | 65.48 | 4.78 | 9.96 | 65.40 | 4.71 | 9.87 |
| 37 | 183.0–185.0 | $C_{23}H_{19}ClFN_3O_3$ | Cl | F | H | H | 62.80 | 4.35 | 9.55 | 62.73 | 4.82 | 9.47 |
| 38 | 195.5–197.0 | $C_{23}H_{19}F_2N_3O_3$ | F | F | H | H | 65.24 | 4.52 | 9.92 | 64.98 | 4.38 | 9.86 |
| 39 | 223.0–224.5 | $C_{23}H_{17}Cl_2F_2N_3O_3$ | F | F | Cl | Cl | 56.11 | 3.48 | 8.54 | 55.96 | 3.38 | 8.51 |
| 40 | 122.5–123.5 | $C_{23}H_{19}Cl_2N_3O_3$ | Cl | Cl | H | H | 60.54 | 4.20 | 9.21 | 59.75 | 4.47 | 7.57 |
| 41 | 219.0–220.5 | $C_{24}H_{20}Cl_1F_2N_3O_3$ | F | F | CH$_3$ | Cl | 61.07 | 4.27 | 8.90 | 60.88 | 4.14 | 8.84 |
| 42 | 238.–240.0 | $C_{24}H_{20}Cl_2F_1N_3O_3$ | F | Cl | CH$_3$ | Cl | 59.03 | 4.13 | 8.60 | 59.65 | 4.09 | 8.63 |
| 43 | 175.0–198.2 | $C_{25}H_{23}Br_1F_2N_4O_3$ | Cl | Cl | Br | —N(CH$_2$)$_2$ | 55.06 | 4.25 | 10.27 | 53.49 | 4.23 | 8.75 |
| 44 | 202.5–205.5° | $C_{25}H_{23}Br_1Cl_2N_4O_3$ | Cl | Cl | Br | —N(CH$_3$)$_2$ | 576.0311[1] | | | 576.0347[1] | | |
| 45 | 192.0–194.0° | $C_{25}H_{24}Br_1Cl_1N_4O_3$ | Cl | H | Br$_3$ | —N(CH$_3$)$_2$ | 55.21 | 4.44 | 10.30 | 55.16 | 4.44 | 10.30 |
| 46 | 168.5–171.5° | $C_{26}H_{26}Cl_1F_1N_4O_3$ | Cl | F | CH$_3$ | —N(CH$_3$)$_2$ | 62.84 | 5.27 | 11.27 | 61.69 | 4.86 | 9.52 |
| 47 | 180.0–183.0° | $C_{26}H_{27}Cl_1N_4O_3$ | G | H | CH$_3$ | —N(CH$_3$)$_2$ | 65.19 | 5.86 | 11.70 | 65.07 | 5.78 | 11.60 |
| 48 | 186.0–187.0° | $C_{25}H_{23}Cl_1F_2N_4O_3$ | F | F | Cl | —N(CH$_3$)$_2$ | 59.94 | 4.63 | 11.19 | 59.23 | 4.40 | 10.72 |
| 49 | 189–191° | $C_{25}H_{24}Cl_2N_4O_3$ | G | H | Cl | —N(CH$_3$)$_2$ | 60.12 | 4.84 | 11.22 | 60.04 | 4.85 | 11.19 |

[1]Exact molecular weight measurement by mass spectrum peak matching technique

TABLE IV

Physical Properties of 1-(2-[2,2-Dimethyl-2,3-dihydro-7-benzofuranyloxy]-5-pyridyl)-3-benzoylureas

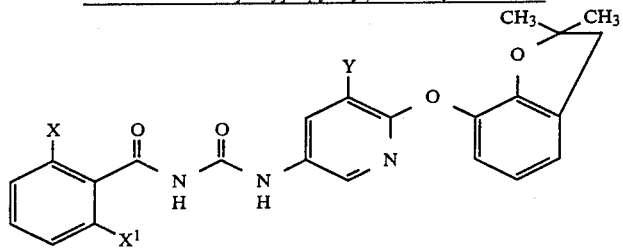

| | | | | | | Elemental Analysis | | | | | |
|---|---|---|---|---|---|---|---|---|---|---|---|
| | | | | | | Calculated | | | Found | | |
| Example | MP °C. | Mol. Formula | X | X[1] | Y | C | H | N | C | H | N |
| 50 | 193–195° | $C_{23}H_{18}BrClFN_3O_4$ | Cl | F | Br | 53.46 | 3.58 | 8.08 | 53.35 | 3.72 | 8.04 |
| 51 | 175.5–176.5 | $C_{23}H_{19}BrClN_3O_4$ | Cl | H | Br | 50.17 | 3.29 | 7.62 | 45.60 | 3.17 | 6.08 |
| 52 | 194.0–198.0 | $C_{23}H_{18}BrCl_2N_3O_4$ | Cl | Cl | Br | 50.17 | 3.29 | 7.62 | 45.60 | 3.17 | 6.08 |
| 53 | 201.0–203.0 | $C_{23}H_{18}BrF_2N_3O_4$ | F | F | Br | 517.0449[1] | | | 517.043[1] | | |

[1]Exact molecular weight measurement by mass spectrum peak matching technique

Certain representative examples of the new compounds were evaluated to determine their pesticidal activity against certain insects, including a caterpillar and a beetle. The new compounds were also tested for phytotoxicity on important economic crops including snapbean, soybean, corn, tomato and cotton. The new compounds were further evaluated for mammalian toxicity.

Suspensions of the test compounds were prepared by dissolving one gram of compound in 50 milliliters of acetone in which had been dissolved 0.1 gram (10 percent of the weight of compound) of a alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described herinbelow were obtained by appropriate dilutions of the stock suspension with water. The test procedures were as follows:

Southern Armyworm Leaf Spray Bait Test

Larvae of the southern armyworm (Spodopteraeridania, (Cram.)), reared on Tendergreen bean plants at a temperature of 80°±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for five days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fouth instar larvae of the Mexican bean beetle (*Epilachna varivestis*, Muls.), reared on Tendergreen bean plants at a temperature of 80°±5° F. and 50±5 percent relative humidity, were the test insects.

The test compounds were fomulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no tes compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5 F., for five days. Although the larvae could easily consume the leaf within 24 to 48 hours, no more food was added. Larvae which were unable to move the length of the body, even upon stimulation, were considered dead.

MITE FOILAGE SPRAY TEST

Adults and nymphal stages of the two-spotted mite (*Tetranychus urticae* Koch) reared on Tendergreen beans under controlled conditions (80+5° F. and 50±5 percent relative humidity). Infested leaves from the stock culture are placed on the primary leaves of 2 bean plants 6–8 inches in height. A sufficient number of mites for testing (150–200) will transfer from the excised leaves to the fresh plants.

Infested Tendergreen bean plants of standard height and age are placed on a revolving turntable. A formulated water mixture of the chemical (100 mL) is applied to the plants by use of a DeVilbiss spray gun with air pressure set at 40 pounds. Application of this volume of formulated compound takes 25 seconds. This volume of spray is sufficient to wet the plants to run-off.

The test compounds are formulated by a standard procedure of solution in acetone, addition of an emulsifier, and dilution with water. Primary spray applications are conducted at 500 ppm.

The treated plants are held at 80±5° F. and 50±5 percent relative humidity for a period of 7 days when mortality counts of motile forms (adults and nymphs) are made.

Microscopic examination of motile forms is made on one leaf from each of the 2 test plants. Any individual which is capable of locomotion upon stimulation is considered living.

MITE LARVACIDAL TEST METHOD

The eggs of the twospotted mite *Tetranychus urticae* (Koch) are obtained from adults reared on Tendergreen beans under controlled conditions (80±5° F. and 50±5 percent relative humidity). Heavily infested leaves from the stock culture are placed on unifested bean plants. Females are allowed to oviposit for a period of 24 hours, and the leaves of the plants are then dipped in a 1000 ppm solution of TEPP in order to kill the motile forms and prevent additional egg laying. TEPP does not affect the viability of the eggs. The TEPPed mited plants are held at 80±5° F. and 50±5 percent relative humidity until the eggs hatch in 3–4 days. Then the larvae are transferred to bean plants 6–8 inches in height. A sufficient number of larvae for testing (50–100) will transfer from TEPP leaves to the fresh plants in 24 hours.

Infested Tendergreen bean plants are placed on a revolving turntable. Test compounds are formulated with DMF, acetone, and a 3 to 1 mixture of Triton 172 and 152, respectively and then diluted in water to appropriate concentrations of chemical for application to the infested plants by use of a DeVilbiss spray gun with air pressure set at 40 pounds. The volume of 100 ml. is sufficient to wet the plants to run off. A blank formulation is used for the control.

The treated plants are held at 80±5° F. and 50±5 percent relative humidity for a period of five to six days, when mortality counts of the larvae are made.

MITE OVICIDE TEST

The egg of the two-spotted mite (*Tetranychus urticae* (Koch) obtained from adults reared on Tendergreen beans under controlled conditions (80±5° F. and 50±5 percent relative humidity). Heavily infested leaves from the stock culture are placed on unifested bean plants. Females are allowed to oviposit for a period of 24 hours, and the leaves of the plants are then dipped in a 1000 ppm solution of TEPP in order to kill the motile forms and prevent additional egg laying. TEPP does not affect the viability of the eggs.

The plants are placed on a revolving turntable. A formulated water mixture of the chemical (100 mL) is applied to the plants by use of a DeVilbiss spray gun with air pressure set at 40 pounds. Application of this volume of formulated compound takes 25 seconds. This volume of spray is sufficient to wet the plants to runoff. An equivalent amount of a water solution containing acetone and emulsifier in the same concentrations as the insecticidal mixture but without the candidate insecticide is also sprayed on the infested plants as a check or control.

The test compounds are formulated by a standard procedure of solution in acetone, addition of an emulsifier, and dilution with water. Primary screening tests are conducted at 500 ppm.

The treated plants are held at 80±5° F. and 50±5 percent relative humidity for 7 days after which counts are made.

Microscopic examination is made of the plant leaves, and the number of unhatched eggs (considered dead) and empty egg shells (living eggs) are noted.

The biological properties of certain respresentative examples of the compounds of this invention are set forth in Tables V and VI.

TABLE V

Biocidal Activity of Representative of Bicyclooxyheterocyclyl Aroyl Ureas Mortality Rating at 500 ppm[3]

| Example | SAW[1] | MBB[2] |
|---|---|---|
| 1 | A | C |
| 2 | A | A |
| 3 | A | A |
| 4 | A | A |
| 5 | C | C |
| 6 | A | A |
| 7 | B | C |
| 8 | A | A |
| 9 | A | A |
| 10 | A | C |
| 11 | A | A |
| 12 | A | A |
| 13 | A | A |
| 14 | A | A |
| 15 | A | A |
| 16 | A | A |
| 17 | A | A |
| 18 | A | A |
| 19 | A | C |
| 20 | A | A |
| 21 | C | C |
| 22 | A | A |
| 23 | A | A |
| 24 | A | A |
| 25 | A | C |
| 26 | A | C |
| 27 | A | C |
| 28 | C | C |
| 29 | A | C |
| 30 | A | C |
| 31 | A | C |
| 32 | C | C |
| 33 | A | A |
| 34 | C | C |
| 35 | C | A |
| 36 | A | A |
| 37 | A | A |
| 38 | C | A |
| 39 | A | A |
| 40 | A | A |
| 41 | A | A |
| 42 | A | A |
| 43 | A | A |
| 44 | A | A |
| 45 | A | A |
| 46 | A | A |
| 47 | A | A |
| 48 | A | A |
| 49 | A | A |
| 50 | C | C |
| 51 | A | C |

[1]Southern Armyworm
[2]Mexican Bean Beetle
[3]Code =
A = 71–100% kill
B = 31–70% kill
C = 0–30% kill

TABLE VI

Activity of Representative Bicyclooxyheterocyclyl Benzoyl Ureas Against Two-Spotted Mite Mortality Rating at 500 ppm[1]

| Example | Adult | Larvae | Egg |
|---|---|---|---|
| 18 | C | A | C |
| 19 | A | A | A |
| 39 | | A | |
| 40 | | A | |

[1]Code =
A = 71–100% kill
B = 31–70% kill
C = 0–30% kill

Although the invention has been illustrated by the foregoing examples, it is not to be construed as being limited to the materials employed therein; but rather, the invention encompasses the generic area as hereinafter disclosed. Various modifications and embodiments can be made without departing from the spirit and scope thereof.

What is claimed is:

1. A compound of the formula:

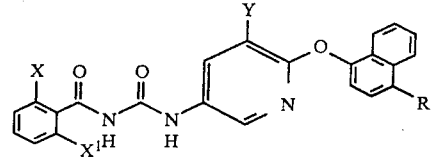

wherein X and X' are halo or lower alkoxy, Y is hydrogen, halo or lower alkyl, and R is hydrogen, halo, or lower alkoxy.

2. A compound of the formula:

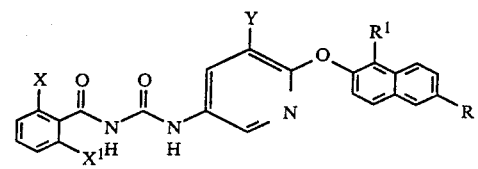

wherein X, Y, R and R¹ are halo and X¹ is hydrogen or halo.

3. A compound of the formula:

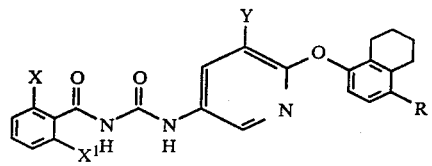

wherein X is halo, X¹ is hydrogen or halo, Y is hydrogen, halo, or lower alkyl, and R is hydrogen, halo or dialkylamino.

4. The compound of claim 1 which is 1-(2-[4-chloro-1-naphthoxy]5-pyridyl)-3-(2,6-difluorobenzoyl) urea.

5. The compound of claim 1 which is 1-(2-[4-chloro-1-naphthoxy]-5-pyridyl)-3-(2-chloro-6-fluorobenzoyl) urea.

6. The compound of claim 1 which is 1-(3-chloro-2-[4-chloro-1-naphthoxy]-5-pyridyl)-3-(2,6-difluorobenzoyl) urea.

7. The compound of claim 1 which is 1-(3-chloro-2-[4-chloro-1-naphthoxy]-5-pyridyl)-3-(2-chloro-6-fluorobenzoyl urea.

8. The compound of claim 1 which is 1-(2-[4-chloro-1-naphthoxy]-3-methyl-5-pyridyl)-3-(2,6-difluorobenzoyl) urea.

9. The compound of claim 1 which is 1-(2-[4-chloro-1-naphthoxy]-3-methyl-5-pyridyl)-3-(2-chloro-6-fluorobenzoyl) urea.

10. The compound of claim 1 which is 1-(3-chloro-2-[4-methoxy-1-naphthoxy]-5-pyridyl)-3-(2,6-difluorobenzoyl) urea.

11. The compound of claim 1 which is 1-(3-methyl 2-[4-methoxy-1-naphthoxy]-5-pyridyl)-3-(2,6-difluorobenzoyl) urea.

12. The compound of claim 2 which is 1-(3-chloro-2-[1,6-dibromo-2-naphthoxy]-5-pyridyl)-3-(2,6-difluorobenzoyl) urea.

13. The compound of claim 2 which is 1-(3-chloro-2-[1,6-dibromo-2-naphthoxy]-5-pyridyl)-3-(2-chloro-6-fluorobenzoyl) urea.

14. The compound of claim 3 which is 1-(3-chloro-2-[4-chloro-5,6,7,8-tetrahydro-1-naphthoxy]-5-pyridyl)-3-(2,6-difluorobenzoyl urea.

15. The compound of claim 3 which is 1-(3-chloro-2-[4-chloro-5,6,7,8-tetrahydro-1-naphthoxy]-5-pyridyl)-3-(2-chloro-6-fluorobenzoyl) urea.

16. A pesticide composition comprising an acceptable carrier and a pesticidally effective amount of the compound of claim 1.

17. A pesticide composition comprising an acceptable carrier and a pesticidally effective amount of the compound of claim 2.

18. A pesticide composition comprising an acceptable carrier and a pesticidally effective amount of the compound of claim 3.

19. A pesticide composition comprising an acceptable carrier and a pesticidally effective amount of the compound of claim 4.

20. A pesticide composition comprising an acceptable carrier and a pesticidally effective amount of the compound of claim 5.

21. A pesticide composition comprising an acceptable carrier and a pesticidally effective amount of the compound of claim 14.

22. A pesticide composition comprising an acceptable carrier and a pesticidally effective amount of the compound of claim 15.

23. A pesticide composition comprising an acceptable carrier and a pesticidally effective amount of the compound of claim 6.

24. A pesticide composition comprising an acceptable carrier and a pesticidally effective amount of the compound of claim 7.

25. A pesticide composition comprising an acceptable carrier and a pesticidally effective amount of the compound of claim 8.

26. A pesticide composition comprising an acceptable carrier and a pesticidally effective amount of the compound of claim 9.

27. A pesticide composition comprising an acceptable carrier and a pesticidally effective amount of the compound of claim 12.

28. A pesticide composition comprising an acceptable carrier and a pesticidally effective amount of the compound of claim 13.

29. A pesticide composition comprising an acceptable carrier and a pesticidally effective amount of the compound of claim 10.

30. A pesticide composition comprising an acceptable carrier and a pesticidally effective amount of the compound of claim 11.

31. A method of controlling pests which comprises subjecting said pests to a pesticidally effective amount of the composition of claim 16.

32. A method of controlling pests which comprises subjecting said pests to a pesticidally effective amount of the composition of claim 17.

33. A method of controlling pests which comprises subjecting said pests to a pesticidally effective amount of the composition of claim 18.

34. A method of controlling pests which comprises subjecting said pests to a pesticidally effective amount of the composition of claim 19.

35. A method of controlling pests which comprises subjecting said pests to a pesticidally effective amount of the composition of claim 20.

36. A method of controlling pests which comprises subjecting said pests to a pesticidally effective amount of the composition of claim 21.

37. A method of controlling pests which comprises subjecting said pests to a pesticidally effective amount of the composition of claim 22.

38. A method of controlling pests which comprises subjecting said pests to a pesticidally effective amount of the composition of claim 23.

39. A method of controlling pests which comprises subjecting said pests to a pesticidally effective amount of the composition of claim 24.

40. A method of controlling pests which comprises subjecting said pests to a pesticidally effective amount of the composition of claim 25.

41. A method of controlling pests which comprises subjecting said pests to a pesticidally effective amount of the composition of claim 26.

42. A method of controlling pests which comprises subjecting said pests to a pesticidally effective amount of the composition of claim 27.

43. A method of controlling pests which comprises subjecting said pests to a pesticidally effective amount of the composition of claim 28.

44. A method of controlling pests which comprises subjecting said pests to a pesticidally effective amount of the composition of claim 29.

45. A method of controlling pests which comprises subjecting said pests to a pesticidally effective amount of the composition of claim 30.

* * * * *